United States Patent [19]

Simpson et al.

[11] 4,090,128
[45] May 16, 1978

[54] APERTURE MODULE FOR USE IN PARTICLE TESTING APPARATUS

[75] Inventors: Ronald O. Simpson; J. David Starling, both of Miami; Bobby D. James, Hialeah; Thomas John Godin, Ft. Lauderdale; Guenter Ginsberg, Miami; Vladimir J. Drbal, Miramar, all of Fla.

[73] Assignee: Coulter Electronics, Inc., Hialeah, Fla.

[21] Appl. No.: 768,864

[22] Filed: Feb. 15, 1977

[51] Int. Cl.² .................. G01N 27/00; G01N 21/00
[52] U.S. Cl. .............................. 324/71 CP; 356/72; 356/39
[58] Field of Search ............ 324/71 CP; 356/72, 102, 356/39; 73/432 PS

[56] References Cited

U.S. PATENT DOCUMENTS

| | | | |
|---|---|---|---|
| 3,622,795 | 11/1971 | Dorman, Jr. | 356/39 X |
| 3,746,976 | 7/1973 | Hogg | 324/71 CP |
| 3,902,115 | 8/1975 | Hogg et al. | 324/71 CP |
| 4,014,611 | 3/1977 | Simpson et al. | 356/72 |

Primary Examiner—Rudolph V. Rolinec
Assistant Examiner—Vincent J. Sunderdick
Attorney, Agent, or Firm—Silverman, Cass & Singer, Ltd.

[57] ABSTRACT

An aperture module for obtaining signals from microscopic particles suspended in a sample blood solution which passes through a scanning aperture. A module housing including an aperture holder is mounted on a container or bath containing a body of the particulate liquid suspension to be tested. The aperture holder with aperture formed therein extends into the vessel to permit passage of the sample through the aperture to an outlet chamber immediately behind the aperture. The chamber is connected to a source of clean electrolyte and has a narrowed or reduced dimension portion positioned immediately behind the aperture. A vacuum is applied to the chamber to cause the sample to be drawn through the aperture for testing thereof. An optical hemoglobinometer is positioned in association with the bath to measure the hemoglobin content of the solution to be tested.

12 Claims, 4 Drawing Figures

APERTURE MODULE FOR USE IN PARTICLE TESTING APPARATUS

CROSS REFERENCE TO RELATED APPLICATION AND PATENTS

This application is related to application Ser. No. 573,265 filed Apr. 30, 1975, now U.S. Pat. No. 4,014,611, issued Mar. 29, 1977 (herein called "the related Patent") for "Aperture Module for use in Particle Testing Apparatus".

The present application also is related in part to the structures disclosed in U.S. Pat. Nos. 3,549,994, 3,580,686, 3,622,795, 3,743,424 and 3,979,669; for purposes of background and detailed description of certain elements referred to herein, these patents are incorporated herein as a part hereof by specific reference.

All of the above patents and application are owned by the same assignee as the present application.

BACKGROUND OF THE INVENTION

1. Field of the Invention

This invention relates generally to the art of studying the physical properties of microscopic particles carried in suspension and more particularly is concerned with structure for analyzing cells in blood by obtaining signals from said cells as they pass through a scanning aperture and also for measuring the hemoglobin content of the blood.

2. Description of the Prior Art

Apparatus for analyzing blood cell particles to determine the size, number and other physical properties thereof are known. Likewise, apparatus are known for measuring the hemoglobin content of blood by use of light-sensitive hemoglobin analysis structure.

The related Patent discloses an aperture module for use in particle testing apparatus which enables analysis of blood cells to determine size, number, etc. thereof. As stated in the related Patent, the module disclosed therein is a practical structure adapted specifically for use in presently developed sophisticated particle analyzing devices; the module is a compact refinement of prior art structures which were not as adaptable for efficient use in the advanced apparatus presently used.

The structure of the related Patent does not, however, include features which permit measurement of the hemoglobin content of the blood sample to be tested. Such additional feature is desirable so that the module, when installed in a particle analyzing apparatus, is capable of performing this additional function without the need for handling the sample twice. The manner of preparing a blood sample for such hemoglobin measurement is described in detail in U.S. Pat. Nos. 3,549,994 and 3,743,424 to which reference may be made for details thereof. In the present application, structure is disclosed for performing hemoglobin content and other analyses and tests of the blood sample using an aperture module which is compact and capable of efficient operation in presently developed particle analyzing apparatus.

SUMMARY OF THE INVENTION

The invention provides an aperture module and bath of the general type disclosed in the Parent Patent for use in particle analyzing apparatus. The module includes an aperture holder for mounting on a vessel or bath containing sample blood solution to be tested. The aperture holder with aperture formed therein extends into the bath to permit passage of the sample through the aperture to an outlet chamber immediately behind the aperture. The chamber is connected to a source of clean electrolyte and has a reduced dimension portion positioned immediately behind the aperture. A vacuum is applied to the chamber through an outlet port positioned in the reduced dimension portion to draw the sample through the aperture for testing thereof. The bath containing the sample is associated with an optical hemoglobinometer for measurement also of the hemoglobin content of the sample.

DESCRIPTION OF THE PREFERRED EMBODIMENT

Figure 1:
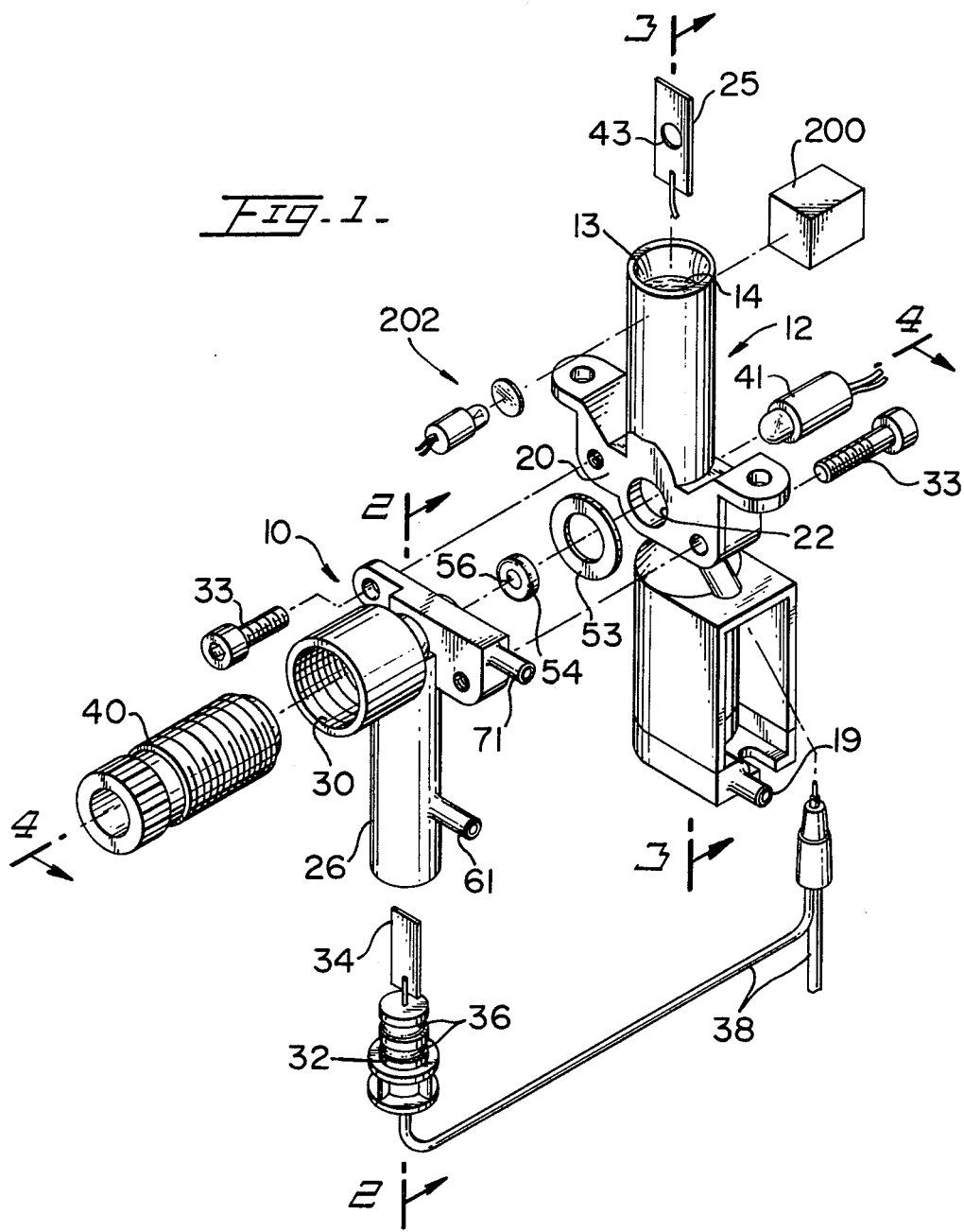
FIG. 1 is an exploded perspective view of the aperture module and bath construction of the invention, there being shown in diagrammatic form an optical hemoglobinometer in association with said bath.

The apparatus with which the aperture module of the invention is intended for uses is known as the Coulter electronic particle analyzing device. (The mark "Coulter" is the Registered Trademark, Registration No. 995,825, of Coulter Electronics, Inc. of Hialeah, Florida). The Coulter device and its principle of operation is referred to with particularity in U.S. Pat. No. 3,549,994 which is incorporated herein by specific reference.

The aperture module of the invention is referred to generally by the reference numeral 10. The module 10 is adapted for mounting or positioning on a container or bath 12 which retains in a chamber 13 thereof a body of blood sample solution 14 to be tested. The bath 12 includes an isolation or drip chamber 101 which also functions as an anti-contamination chamber as described hereinafter. The chamber 13 is connected to isolation chamber 101 by a passageway 100 having a nozzle part 102; a drain port 19 is provided at the bottom of the isolation chamber 101. One side wall 20 of the bath 12 has an opening 22 to the interior of the chamber 13.

The aperture module 10 is comprised of a housing part 26 with two chambers 28, 30 formed therein normal with respect to each other. Chamber 28 has a blind end 29 and is adapted for receipt in open end 31 of an electrode cable assembly 32 which carries a common or grounded electrode 34 for the Coulter device of which the module forms a part. (A signal electrode 25 is provided in chamber 13 of bath 12 as required in such device.) The cable assembly 32 is sealingly engaged in chamber 28 by any suitable means such as O-rings 36 to prevent escape of fluid from open end 31 of the chamber. Electric leads 38 couple the electrodes 25, 34 with the detector (not shown) of the Coulter device.

Figure 4:
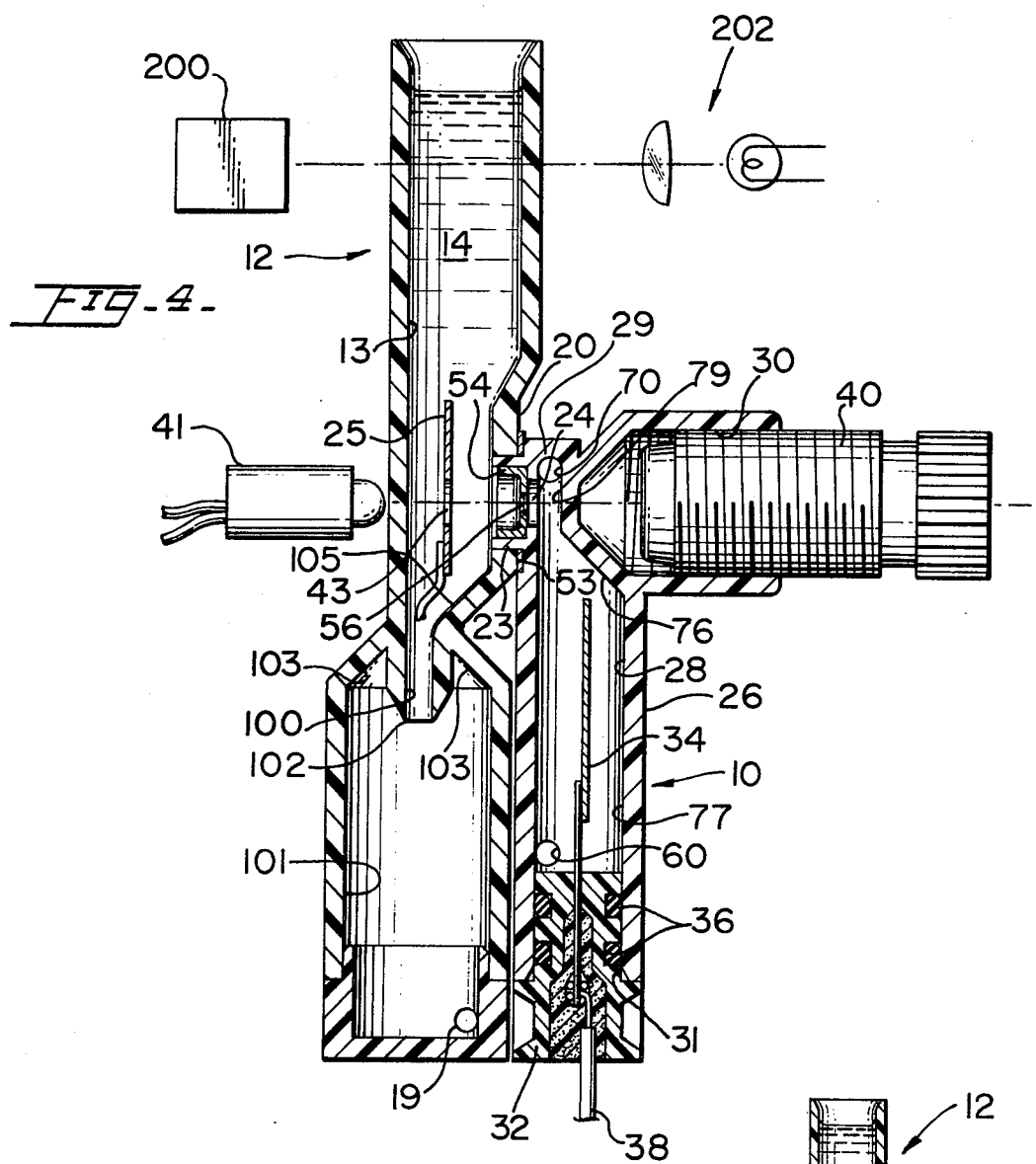
FIG. 4 is a sectional view taken along the line 4—4 of FIG. 1 in the direction indicated generally with the exploded elements in assembled condition.
Figure 2:
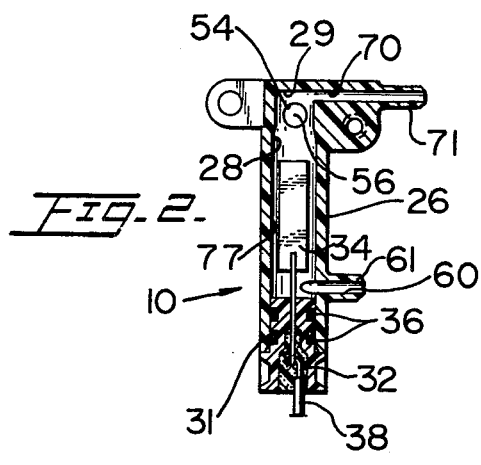
FIG. 2 is a sectional view taken along the line 2—2 of FIG. 1 in the direction indicated generally with the exploded elements in assembled condition.
Figure 3:
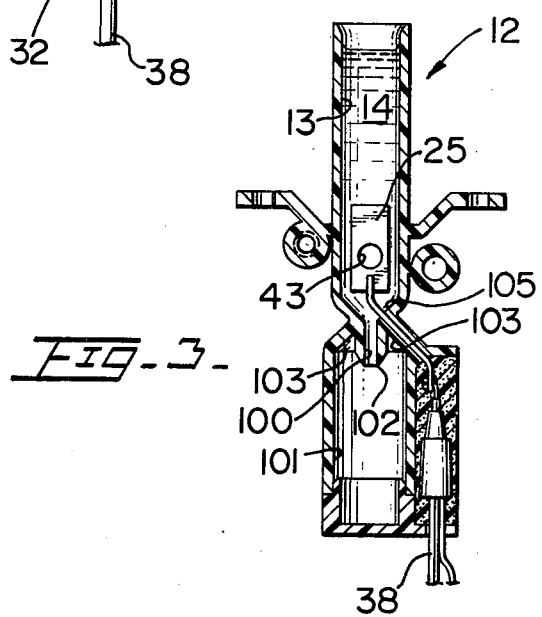
FIG. 3 is a sectional view taken along the line 3—3 of FIG. 1 in the direction indicated generally with the exploded elements in assembled condition.

Chamber 30 projects within chamber 28 and terminates at a sloped portion 76 of wall 77 of chamber 28 (see FIG. 4). The sloped portion 76 defines a narrowed part 79 of chamber 28 which leads to the blind end 29 thereof. Chamber 30 is adapted for receipt of objective lens assembly 40 which is provided for visually examining the actual opening of the aperture wafer of the module while it is in use. An optical light source 41 is positioned coaxially with the lens assembly 40 adjacent bath 12 to provide illumination for viewing through the lens. Electrode 25 in bath 12 has an opening 43 so that the light from source 41 may pass to the lens.

The entire construction of the aperture module and bath preferably is formed of transparent synthetic resin or other material which will transmit light with as little distortion as possible. The module 10 has formed thereon coaxially with chamber 30 an annular boss 23 having a passageway 24 communicating with the chamber 28. An aperture wafer or disc 54 is secured within boss 23 by cement or other suitable means. The disc 54 is provided with aperture 56 formed therein in a known manner.

As illustrated in the figures, the external configuration of boss 23 corresponds generally to opening 22 in bath 12 such that the module 10 is mountable upon the bath by telescopically engaging the boss within the opening 22. A washer 53 positioned around the boss 23 between bath 12 and aperture module 10 seals the juncture to prevent fluid leakage therethrough. The aperture module 10 and bath 12 may further be secured together by screws 33 cojoining the same.

Aperture module 10 has an input port 60 proximate the bottom of chamber 28 and an output port 70 located in the upper narrowed portion of the chamber; each of the ports 60, 70 have respective fittings 61, 71 projecting therefrom normal to the chamber 28. The cross-sectional dimension of the narrowed portion 79 of chamber 28 and the diameter of output port 70 are approximately identical such that port 70 completely fills the said narrowed portion.

As shown schematically in FIGS. 1 and 4, a hemoglobin measuring device 200 is associated with the upper portion of bath 12. The device 200 includes a light source and lens system 202 indicated diagrammatically and constructed and arranged according to the teachings of U.S. Pat. Nos. 3,549,994 and 3,622,795 incorporated herein. The device 200 will measure the hemoglobin content of the blood sample 14 which is introduced to the bath.

The operation of the hemoglobin measuring device 200 and the aperture module preferably is as follows:

Sample 14 is introduced to chamber 13 of bath 12 to commence automatic sequencing of the testing operations by control means (not shown). A vacuum is applied to output port 70 to draw clean electrolyte from a supply (not shown) through input port 60 and into chamber 28. The input port 60 is opened for a short period of time of about one second so that the clean electrolyte sweeps through chamber 28 to clean or rinse the same. Input port 60 thereafter is closed. The hemoglobin content of sample 14 thereupon is measured by operation of device 200. Closing of the input port 60 causes the sample 14 to be drawn through the aperture 56 to be sensed by the Coulter analyzing device. The sample 14 passes into the narrowed portion of chamber 28 and upward and out through exit port 70 to complete the cycle after which the vacuum at port 70 is turned off.

In the above-described sequence of operation, sample 14 moves through the aperture 56 at the same time that the hemoglobin measuring device 200 is operating; however, preferably the sensing of the sample by the Coulter analyzing device does not then take place because the signals involved in the measuring of the hemoglobin content of the sample may cause interference with the signals to be sensed by the Coulter analyzing device. Hence, these two forms or trains of signals should not occur at the same time.

An alternate sequence of operation may be used in which the hemoglobin measurement by device 200 takes place at the very end of the cycle, after the sample is sensed by the Coulter analyzing device and after the vacuum at port 70 is turned off and just prior to the time clean electrolyte is swept through chamber 28. This sequence of operation may have the advantage of permitting the sample 14 in bath 12 to have settled and not be turbulent. Also, if the hemoglobin measurement takes place at a time when the vacuum is not applied at port 70, there may be even less turbulence in the bath chamber 13.

The design of the aperture module 10 and bath 12 as disclosed herein is such as to provide several advantageous features over structures previously known. Prior to each sample testing operation of the device, it is desired to flush or sweep the chamber 28 clean and introduce fresh electrolyte thereto. During this flushing or sweeping operation, input port 60 is opened to the electrolyte supply and vacuum is applied to output port 70. The electrolyte in chamber 28 thereupon is drawn up through chamber 28, past electrode 34, the sloped wall 76 and the zone immediately behind the aperture 56 to remove air bubbles and undesirable materials which may have accumulated in the chamber and on the electrode. This latter described sweep flow operation preferably is applied intermittently with the sensing of the sample by the Coulter analyzing device, i.e., when particle analysis is not being made. The sloping surface 76 and the fact that the exit end of chamber 28 is only as large as the exit port 70 both reduces the tendency of bubbles forming in the chamber and prevents bubbles from remaining in the zone behind the aperture; such bubbles are carried away through port 70 during the sweeping operation.

As stated, electrode 34 is the common or grounded electrode of the device in which module 10 is intended for use, and electrode 25 in bath 12 is the signal or electrically hot electrode. This positioning of the electrodes is preferred because hydrogen bubbles tend to form on the grounded electrode. Positioning the grounded electrode 34 on the downstream side of the aperture prevents such bubbles from passing through the aperture thereby creating undesirable extraneous signals. Further, since the grounded electrode 34 is positioned on the downstream side of the aperture, the same can be cleaned by the sweep flow operation described above.

Positioning the signal or hot electrode on the upstream side of the aperture in bath 12 renders it desirable to have an electrical isolation chamber on said upstream side. It also is desirable to provide a drip chamber in association with the sample chamber 13 to prevent contamination of the sample by prior liquids introduced into the bath 12 as discussed in U.S. Pat. No. 3,580,686 incorporated herein. The single chamber 101 satisfies the need for both an electrical isolation chamber and anti-contamination chamber.

Chamber 101 is provided with input nozzle 102 from chamber 13; nozzle 102 is separated from the side walls of chamber 101 by reason of the sloped wall portions 103 thereof. The side wall portions 103 therefore terminate above the lower end of the nozzle 102 to provide the necessary electrical isolation for the drip chamber.

The chamber 101 functions also as an anti-contamination chamber by reason of the reduced dimension neck portion 105 of sample chamber 13 at the juncture thereof with passageway 100 leading to chamber 101. The neck portion 105 is formed free of abrupt discontinuities in accordance with the teachings of U.S. Pat. No. 3,580,686. As sample is introduced to chamber 13, the first few drops thereof flow over the entire inner surface of the chamber and carry downwardly in a rinsing action any residue from prior liquids or the like. As an additional anti-contamination feature, the drain port 19 is located off-centered at the bottom of chamber 101; this off-center feature of the drain prevents any spit-up of liquid which may occur from the drain area directly back upwardly into the passageway 100. Drain port 19 is opened at the end of a complete cycle of operation of the device at which time rinsing of the chamber 101 may be desired.

Minor variations in the structure and other variations in the arrangement and size of the various parts may occur to those skilled in the art without departing from the spirit or circumventing the scope of the invention as set forth in the appended claims.

What it is desired to secure by Letters Patent of the United States is:

1. An aperture module for use in particle testing apparatus including a container of particulate liquid suspension to be tested, said module comprising, a housing formed of optically clear material and having a first chamber and a second chamber, an aperture holder disposed in the first chamber and having an aperture provided therein, the aperture holder extending into the container with the aperture in communication on one side thereof with the liquid suspension, said first chamber having a wall defining a reduced dimension portion and the aperture being in communication on the side opposite said one side with said reduced dimension portion, a first electrode in the container and a second electrode in the first chamber to establish an electrical field in the aperture between the container and the aperture module, means for connecting the first chamber at an entrance thereof to a source of particle free liquid and means for connecting the reduced dimension portion of the first chamber to fluid moving means to move the suspension from the container through the aperture into the reduced dimension portion of the first chamber, means including electrical leads connected to said electrodes and adapted to extend connections to a detector to respond to electrical measuring signals produced across said electrodes with passage of particles through said aperture, and an objective lens assembly positioned in the second chamber adjacent said wall defining the reduced dimension portion of the first chamber for visually examining the aperture during movement of the suspension therethrough.

2. An aperture module as claimed in claim 1 in which said aperture holder includes an annular boss extending from and opening to the first chamber, an aperture disc retained in the boss and the aperture being formed in the disc.

3. An aperture module as claimed in claim 1 in which the container is a bath having a side wall with at least one opening to the interior thereof, the opening on said side wall being of configuration to permit telescopic mating engagement of the boss therein.

4. An aperture module as claimed in claim 1 in which said first chamber and said second chamber are disposed normal with respect to each other, said second chamber projecting into said first chamber and terminating at a sloped portion of the wall of said first chamber.

5. An aperture module as claimed in claim 1 in which said reduced dimension portion of the first chamber terminates at a blind end and said means for connecting the first chamber to fluid moving means include an output port opening to the blind end.

6. An aperture module as claimed in claim 5 in which the cross-sectional dimension of the blind end and the diameter of the outlet port are approximately identical such that the port completely occupies the outlet area of the reduced dimension portion.

7. An aperture module as claimed in claim 1 in which the container includes a combined sample chamber and a drip chamber, a passageway connecting said sample chamber with said drip chamber, the passageway terminating with a nozzle, and a drain port opening to the drip chamber.

8. An aperture module as claimed in claim 7 in which the drain port is positioned off-centered at the bottom of the drip chamber.

9. An aperture module as claimed in claim 7 in which the sample chamber has a reduced-dimension neck portion loading to the passageway,.

10. An aperture module as claimed in claim 7 in which the walls of the drip chamber are sloped proximate the opening of the passageway therein and said sloped walls terminate above the lower end of said nozzle.

11. An aperture module as claimed in claim 1 in which the liquid suspension to be tested is a blood sample, said container having associated therewith an optical hemoglobinometer for measuring the hemoglobin content of the blood sample in the container.

12. An aperture module as claimed in claim 1 including means to sweep the particle free liquid through the first chamber to clean the same intermittently with movement of the suspension through the aperture.

* * * * *